(12) United States Patent
Cheng

(10) Patent No.: US 6,190,329 B1
(45) Date of Patent: Feb. 20, 2001

(54) THERMOSCAN HAVING VOICE AND INFRARED COMMUNICATION INTERFACE

(75) Inventor: Chien-Chung Cheng, Taipei (TW)

(73) Assignee: Draco Tech International Corp., Taipei (TW)

( * ) Notice: Under 35 U.S.C. 154(b), the term of this patent shall be extended for 0 days.

(21) Appl. No.: 09/273,020

(22) Filed: Mar. 19, 1999

(51) Int. Cl.$^7$ .................................................. A61B 5/00
(52) U.S. Cl. ........................................... 600/549; 600/559
(58) Field of Search ................................... 600/474, 483, 600/500, 502, 503, 549, 559, 587, 595

(56) References Cited

U.S. PATENT DOCUMENTS

| | | | |
|---|---|---|---|
| 5,211,479 | * | 5/1993 | Coffey et al. .......................... 374/151 |
| 5,246,292 | * | 9/1993 | Gal et al. .............................. 600/549 |
| 5,473,629 | * | 12/1995 | Muramoto ............................ 600/549 |
| 5,873,833 | * | 2/1999 | Pompei ................................ 600/549 |

* cited by examiner

Primary Examiner—Max Hindenburg
(74) Attorney, Agent, or Firm—Pro-Techtor International Services

(57) ABSTRACT

A thermoscan having a main body provided with a single-chip central processing unit to which a temperature sensing circuit, a heartbeat sensing circuit, a bulb driving circuit, a liquid crystal display (LCD), a memory for storing programs, and a communication interface including a voice chip and infrared transmission means are electrically connected. The heartbeat sensing circuit detects a patient's heartbeats from capillary pulse at the patient's finger, the bulb driving circuit actuates an illuminant in the main body of the thermoscan to illuminate and therefore facilitate inspection of the patient's acoustic meatus. The liquid crystal display and the voice chip together enable visual and voice indications of a canned temperature at the same time. And, the infrared transmission means enables data communication between the thermoscan and an externally connected personal computer or microcomputer.

9 Claims, 3 Drawing Sheets

THERMOSCAN HAVING VOICE AND INFRARED COMMUNICATION INTERFACE

BACKGROUND OF THE INVENTION

The present invention relates to a thermoscan, and more particularly to a thermoscan having voice and infrared communication interface and capable of detecting a patient's heartbeats and illuminating the patient's acoustic meatus to facilitate inspection thereof.

The thermoscan disclosed in the present invention is developed by making improvement to the thermoscan disclosed in U.S. patent application Ser. No. 09/231,543 entitled "A Voice Thermoscan" also filed in the name of the applicant. The U.S. patent application Ser. No. 09/231,543 discloses a thermoscan having a main body in which a sensing means, a micro processor, a liquid crystal display, and an electronic erasable programmable read-only memory (EEPROM) are provided. The sensing means senses an infrared temperature at a body temperature point on a patient's eardrum and sends out a corresponding signal that is sampled and digitized by the micro processor and then operated and compared with corrected data stored in the EEPROM. A confirmed temperature value for the sensed infrared temperature is output to a communication interface that includes voice and infrared transmission means. The voice means enables voice indication of the confirmed temperature value and the infrared transmission means converts the temperature value into an approved communication protocol for transmission and then transmits the temperature data to an external microcomputer or a personal computer.

While the thermoscan disclosed in U.S. patent application Ser. No. 09/231,543 is practical for use, it would be even better if the thermoscan is provided with means for illuminating a patient's acoustic meatus to facilitate inspection thereof without the need of fetching another separate illuminating tool. Furthermore, since the thermoscan is now widely used by general consumers to scan body temperature conveniently, it would be more practical for use if it is provided with other functions, such as detecting a user's heartbeats.

SUMMARY OF THE INVENTION

It is therefore a primary object of the present invention to provide a thermoscan having voice and infrared communication interface that enables not only digitized and voiced indication of scanned body temperature value at the same time as disclosed in U.S. patent application Ser. No. 09/231,543, but also convenient heartbeat detection. Information about the scanned body temperature and the detected heartbeats can be transmitted to and stored in an externally connected personal computer or microcomputer via the existing infrared transmission means in the thermoscan, whereby a databank for such information may be established to effectively keep family health records for future check and follow-up.

Another object of the present invention is to provide a thermoscan having voice and infrared communication interface that enables not only digitized and voiced indication of scanned body temperature value at the same time as disclosed in U.S. patent application Ser. No. 09/231,543, but also convenient acoustic meatus illumination to facilitate inspection thereof.

To achieve the above and other objects, the thermoscan of the present invention has a main body provided with a single-chip central processing unit to which a temperature sensing circuit, a heartbeat sensing circuit, a bulb driving circuit, a liquid crystal display (LCD), a memory for storing programs, and a communication interface including a voice chip and infrared transmission means are electrically connected. The liquid crystal display and the voice chip together enable visual and voice indication of a scanned temperature value at the same time, and the infrared transmission means enables conversion of a scanned temperature into an approved communication protocol for transmitting the temperature data to an externally connected personal computer or microcomputer. The thermoscan is characterized in that the heartbeat sensing circuit detects a patient's heartbeats from capillaries at the patient's fingers and the detected heartbeats may be shown in the liquid crystal display and/or voiced through the voice chip and stored in the external computer via the infrared transmission means, and that the bulb driving circuit actuates an illuminant in the main body of the thermoscan to illuminate and therefore facilitate inspection of the patient's acoustic meatus.

BRIEF DESCRIPTION OF THE DRAWINGS

The objects, features, and functions of the present invention may be best understood by referring to the following detailed description of the preferred embodiments and the accompanying drawings, wherein.

DETAILED DESCRIPTION OF THE PREFERRED EMBODIMENTS

Figure 1:
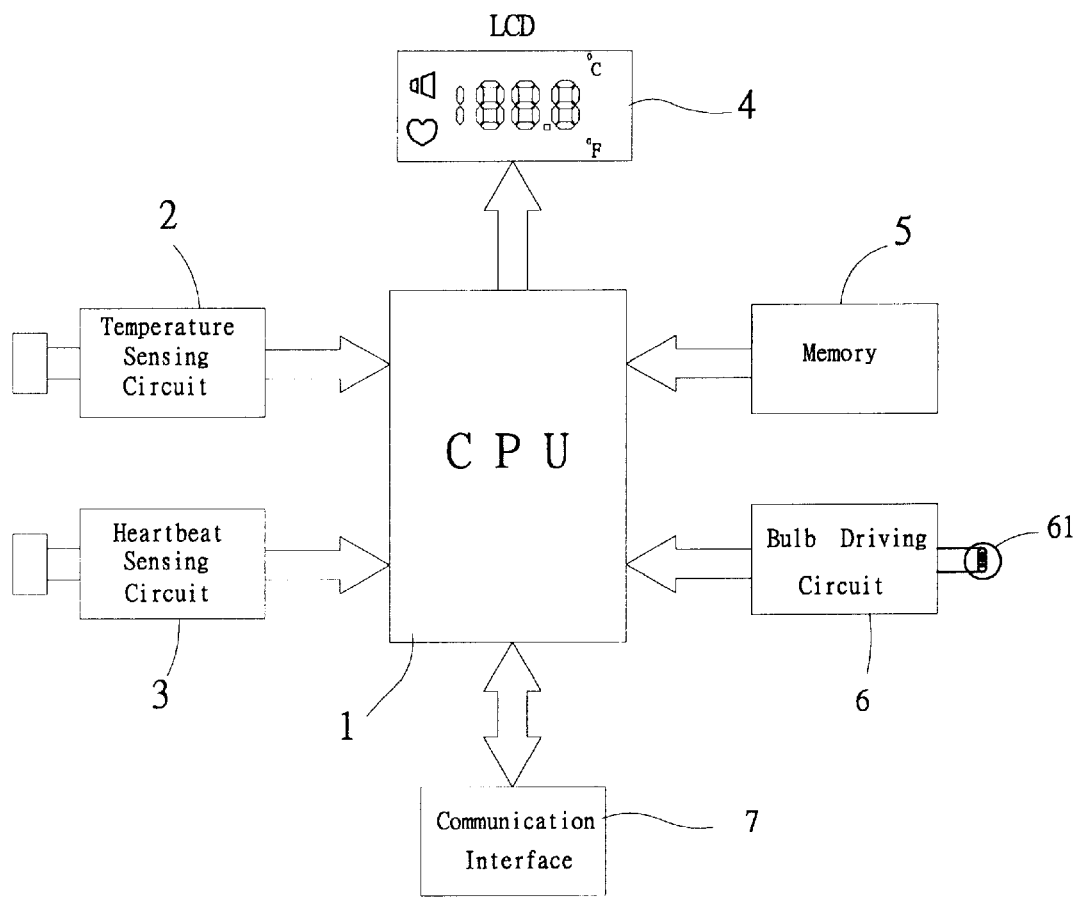
FIG. 1 is a block diagram of the system of the present invention.

Please refer to FIG. 1 that is a block diagram showing a system for a thermoscan having voice and infrared communication interface according to the present invention. As shown in the drawing, the thermoscan has a main body provided with a single-chip central processing unit (CPU) 1 to which a temperature sensing circuit 2, a heartbeat sensing circuit 3, a liquid crystal display (LCD) 4, a memory 5 for storing programs, a bulb driving circuit 6, and a communication interface 7 including a voice chip and infrared transmission means are electrically connected.

The CPU 1 includes an internal 14-bit A/D (analog-digital) LCD driving circuit that is capable of converting analog signals from the temperature sensing circuit 2 and the heart-beat sensing circuit 3 into digits.

The temperature sensing circuit 2 cooperates with a temperature difference thermopile element to scan a temperature at a patient's eardrum.

The heartbeat sensing circuit 3 is capable of detecting a patient's heartbeats based on capillary pulse at the patient's finger.

The liquid crystal display 4 is capable of displaying digits indicating values of the scanned temperature and the detected number of heartbeats.

The memory 5 has corrected digital data obtained from the temperature sensing circuit 2 and the heartbeat sensing circuit 3 stored therein. In the present invention, the memory 5 may be an EEPROM.

The bulb driving circuit 6 is capable of driving a bulb 61 provided in the main body of the thermoscan.

The communication interface 7 has a voice chip and infrared transmission means included therein. The voice chip cooperates with a digital to analog (D/A) conversion circuit to output analog signals to a speaker provided inside the main body of the thermoscan. The infrared transmission means is capable of transmitting infrared (IR) data to facilitate communication of related data between the CPU 1 and an externally connected microcomputer or personal computer.

Figure 2:
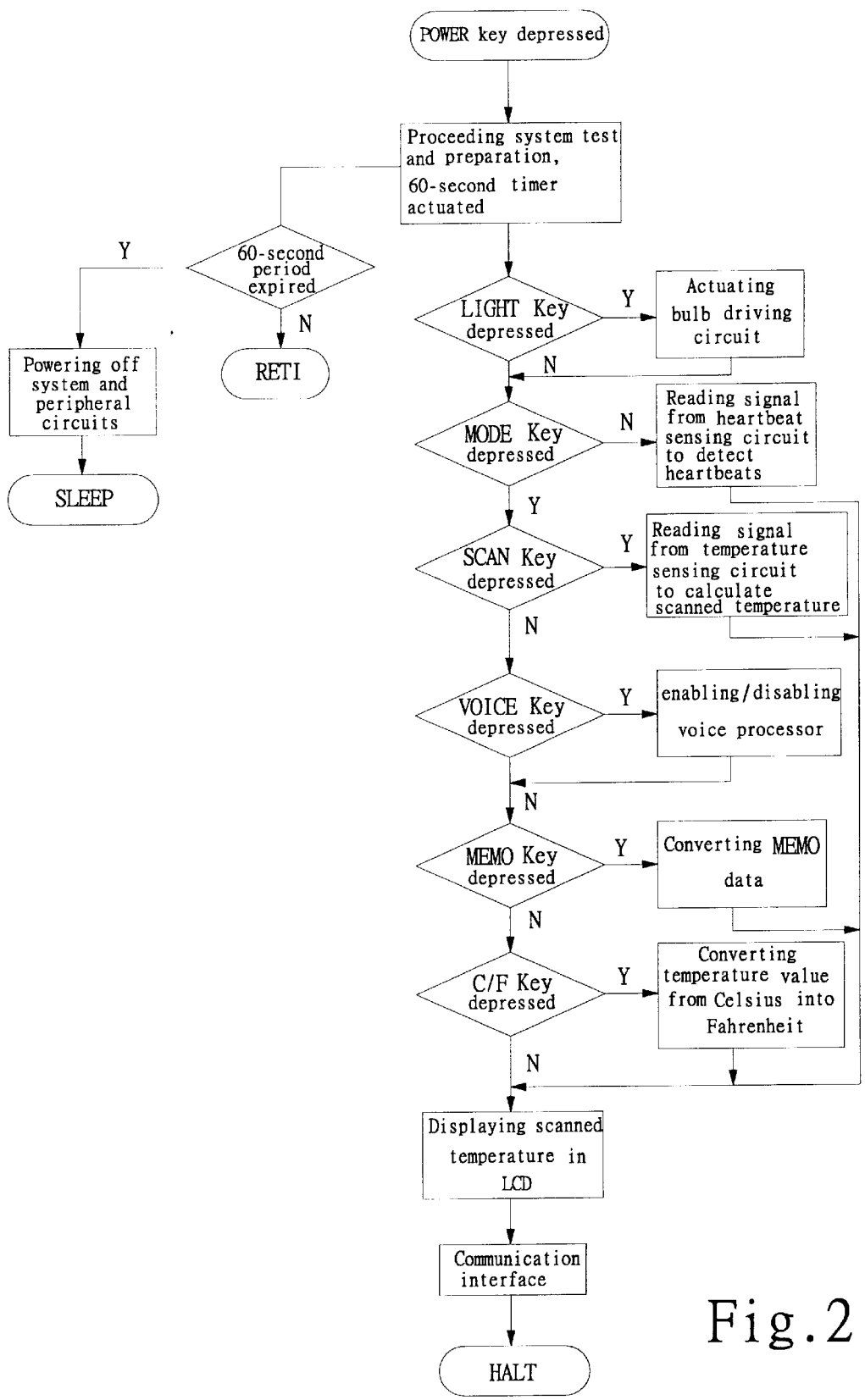
FIG. 2 is a flowchart of the system operational procedures of the present invention.

Please refer to FIG. 2 that is a flowchart of system operational procedures of the thermoscan according to the present invention. Possible operations included in the system of the thermoscan are:

a. Depressing of a POWER key so that the system is powered on. After the system is started and a LIGHT key is depressed, the bulb 61 will be driven by the CPU 1 through an appropriate program stored in the memory 5 to lighten for ten seconds and then extinguishes automatically;

b. Depressing of a MODE key so that a value provided by the heartbeat sensing circuit 3 is read by the CPU 1 through an appropriate program stored in the memory 5. The value read is then compared and calculated to display number of heartbeats in the liquid crystal display 4;

c. Depressing of a SCAN key so that a value provided by the temperature sensing circuit 2 is read by the CPU 1 through an appropriate program stored in the memory 5. After an analog to digital conversion, the value read is converted into a body temperature and displayed in the liquid crystal display 4;

d. Depressing of a VOICE key so that the CPU 1 uses an appropriate program stored in the memory 5 to cause a voice and synchronization circuit in the communication interface 7 to correctly voice out the digits shown in the liquid crystal display 4 via the speaker. Moreover, the infrared transmission means transmits infrared data to an externally connected computer for communication purpose;

e. Depressing of a MEMO key so that the CPU 1 would immediately memorize a currently obtained value or show previously recorded data in the liquid crystal display 4;

f. Depressing of a C/F key so that the CPU 1 uses an appropriate program stored in the memory 5 to convert a Celsius temperature value into a Fahrenheit temperature value and show the latter in the liquid crystal display 4; and g. The system automatically powers off when there is not any other key depressed within 60 seconds after the last operation.

Figure 3:
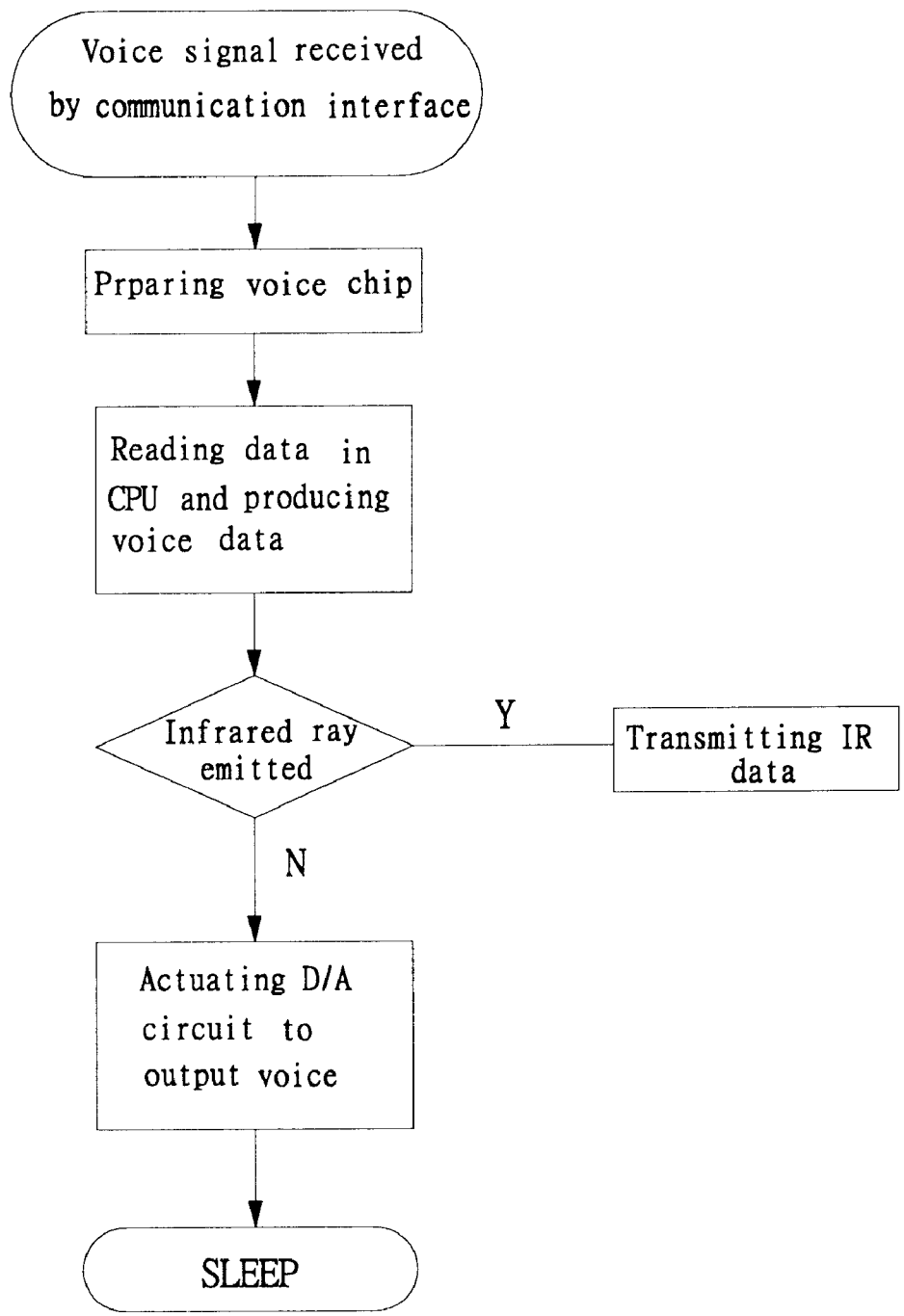
FIG. 3 is a flowchart of the operational procedures of the communication interface of the present invention.

FIG. 3 is a flowchart of operational procedures of the communication interface 7 included in the present invention. As shown, the voice chip included in the communication interface 7 cooperates with the D/A conversion circuit to output an analog signal representing a scanned temperature or detected heartbeat value to the speaker inside the main body of the thermoscan, so that voice corresponding to the scanned temperature or detected heartbeats is sounded. And, the infrared transmission means included in the communication interface 7 converts the scanned temperature or detected heartbeat value into a corresponding communication protocol and transmits the same to an externally connected microcomputer or a personal computer.

It is to be noted that the CPU 1 is not necessarily limited to a single-chip CPU. For example, by taking advantage of a form of ASIC, any and all peripheral elements needed by the CPU 1, such as the driving circuit for the liquid crystal display 4, the A/D and D/A conversion circuits, and the voice circuit, can be included in one single chip to achieve the same objects and functions without departing from the spirit of the present invention.

Furthermore, the bulb driving circuit 6 mentioned in the illustrated embodiment of the present invention is intended for driving the bulb 61, so that the bulb 61 emits light for illuminating a patient's acoustic meatus. It is to be noted that the present invention is not necessarily limited to use the bulb 61 as an illuminating means. Any other illuminant capable of providing sufficient light to illuminate the acoustic meatus, such as a light emitting diode (LED), should also be covered by the spirit of the present invention.

With the above description, it can be easily understood that the present invention is improved in comparison with the U.S. patent application Ser. No. 09/231,543 while providing new functions of detecting the heartbeats and illuminating the acoustic meatus. The present invention is therefore novel in design and practical for use.

What is claimed is:

1. A thermoscan having voice and infrared communication interface, comprising a main body provided at an inner space with a single-chip central processing unit to which a temperature sensing circuit, a heartbeat sensing circuit, a liquid crystal display (LCD), a memory for storing programs, and a communication interface including a voice chip and infrared transmission means are electrically connected; said liquid crystal display and said voice chip together enabling visual and voice indications of a scanned temperature at the same time, and said infrared transmission means converting a value of said scanned temperature into a corresponding communication protocol in order to transmit said temperature value to an external hardware connected to said thermoscan, such as a microcomputer or a personal computer; said heartbeat sensing circuit allowing said thermoscan to detect a patient's heartbeats from capillary pulse at the patient's finger, and information about detected heartbeats being either displayed in said liquid crystal display or voiced through said voice chip, and being optionally transmitted to the externally connected hardware through said infrared transmission means.

2. A thermoscan having voice and infrared communication interface as claimed in claim 1, wherein said central processing unit has a bulb driving circuit connected thereto for driving an illuminant provided in said main body of said thermoscan.

3. A thermoscan having voice and infrared communication interface as claimed in claim 2, wherein said illuminant is a bulb.

4. A thermoscan having voice and infrared communication interface as claimed in claim 2, wherein said illuminant is a light emitting diode.

5. A thermoscan having voice and infrared communication interface as claimed in claim 1, further comprising peripheral elements required by said central processing unit, and said peripheral elements including a liquid crystal display driving circuit, an analog to digital conversion circuit, a digital to analog circuit, and a voice circuit, and being included in one single chip in the form of ASIC.

6. A thermoscan having voice and infrared communication interface, comprising a main body provided at an inner space with a single-chip central processing unit to which a temperature sensing circuit, a bulb driving circuit, a liquid crystal display (LCD), a memory for storing programs, and a communication interface including a voice chip and infrared transmission means are electrically connected; said liquid crystal display and said voice chip together enabling visual and voice indications of a scanned temperature at the same time, and said infrared transmission means converting a value of said scanned temperature into a corresponding communication protocol in order to transmit said temperature value to an external hardware connected to said thermoscan, such as a microcomputer or a personal computer; said bulb driving circuit driving an illuminant provided in said main body of said thermoscan, whereby said illuminant may be separately actuated to illuminate a patient's acoustic meatus for inspection purpose.

7. A thermoscan having voice and infrared communication interface as claimed in claim 6, wherein said illuminant is a bulb.

8. A thermoscan having voice and infrared communication interface as claimed in claim 6, wherein said illuminant is a light emitting diode.

9. A thermoscan having voice and infrared communication interface as claimed in claim 6, further comprising peripheral elements required by said central processing unit, and said peripheral elements including a liquid crystal display driving circuit, an analog to digital conversion circuit, a digital to analog circuit, and a voice circuit, and being included in one single chip in the form of ASIC.

* * * * *